(12) United States Patent
Guterman

(10) Patent No.: US 8,480,557 B2
(45) Date of Patent: *Jul. 9, 2013

(54) NONAUGMENTIVE MASTOPEXY

(75) Inventor: Lee R. Guterman, Amherst, NY (US)

(73) Assignee: Refine, LLC, Santa Rosa, CA (US)

( * ) Notice: Subject to any disclaimer, the term of this patent is extended or adjusted under 35 U.S.C. 154(b) by 1198 days.

This patent is subject to a terminal disclaimer.

(21) Appl. No.: 11/782,839

(22) Filed: Jul. 25, 2007

(65) Prior Publication Data

US 2008/0027273 A1 Jan. 31, 2008

Related U.S. Application Data

(60) Provisional application No. 60/820,565, filed on Jul. 27, 2006.

(51) Int. Cl.
*A61F 2/12* (2006.01)

(52) U.S. Cl.
USPC .......................................................... 600/37

(58) Field of Classification Search
USPC ..................................... 600/37; 128/897, 898
See application file for complete search history.

(56) References Cited

U.S. PATENT DOCUMENTS

| | | | |
|---|---|---|---|
| 4,372,293 A | 2/1983 | Vijil-Rosales | |
| 4,840,629 A | 6/1989 | Bustos | |
| 5,584,884 A | 12/1996 | Pignataro | |
| 5,676,161 A | 10/1997 | Breiner | |
| 5,910,124 A | 6/1999 | Rubin | |
| 6,110,101 A | 8/2000 | Tihon et al. | |
| 6,203,570 B1 | 3/2001 | Baeke | |
| 6,210,439 B1 | 4/2001 | Firmin et al. | |
| 6,402,585 B1 | 6/2002 | Gatto et al. | |
| 6,464,726 B1 | 10/2002 | Heljenek | |
| 6,695,855 B1 | 2/2004 | Gaston | |
| 6,908,473 B2 | 6/2005 | Skiba et al. | |
| 6,960,160 B2 | 11/2005 | Browning | |
| 7,081,129 B2 | 7/2006 | Chobotov | |
| 7,837,613 B2 * | 11/2010 | Lashinski et al. | 600/37 |
| 2002/0029011 A1 | 3/2002 | Dyer | |
| 2002/0143234 A1 | 10/2002 | LoVuolo | |
| 2004/0106847 A1 | 6/2004 | Benderev | |
| 2005/0090827 A1 | 4/2005 | Gedebou | |
| 2005/0240224 A1 | 10/2005 | Wu | |
| 2006/0030939 A1 | 2/2006 | Frank | |
| 2006/0036333 A1 | 2/2006 | Smith et al. | |
| 2006/0069403 A1 | 3/2006 | Shalon | |
| 2006/0074314 A1 | 4/2006 | Slayton et al. | |
| 2006/0089525 A1 | 4/2006 | Mamo et al. | |
| 2006/0167338 A1 | 7/2006 | Shfaram | |
| 2006/0201519 A1 | 9/2006 | Frazier et al. | |
| 2007/0055095 A1 | 3/2007 | Chu et al. | |
| 2007/0156175 A1 * | 7/2007 | Weadock et al. | 606/216 |
| 2008/0027486 A1 | 1/2008 | Jones et al. | |
| 2008/0082113 A1 | 4/2008 | Bishop et al. | |

FOREIGN PATENT DOCUMENTS

WO WO 03/103536 A2 * 12/2003

OTHER PUBLICATIONS

U.S. Appl. No. 12/400,751, filed Mar. 9, 2009, Saint et al.

* cited by examiner

*Primary Examiner* — Samuel Gilbert
(74) *Attorney, Agent, or Firm* — Knobbe, Martens, Olson & Bear LLP

(57) ABSTRACT

Disclosed are methods and devices for minimally invasive mastopexy, or other soft tissue suspension, which may be accomplished with our without augmentation.

18 Claims, 12 Drawing Sheets

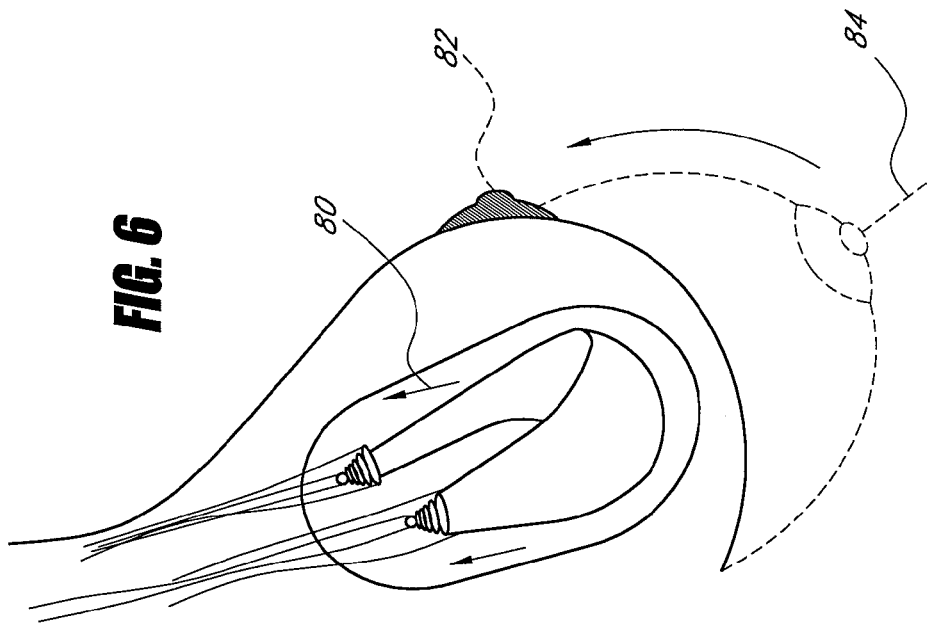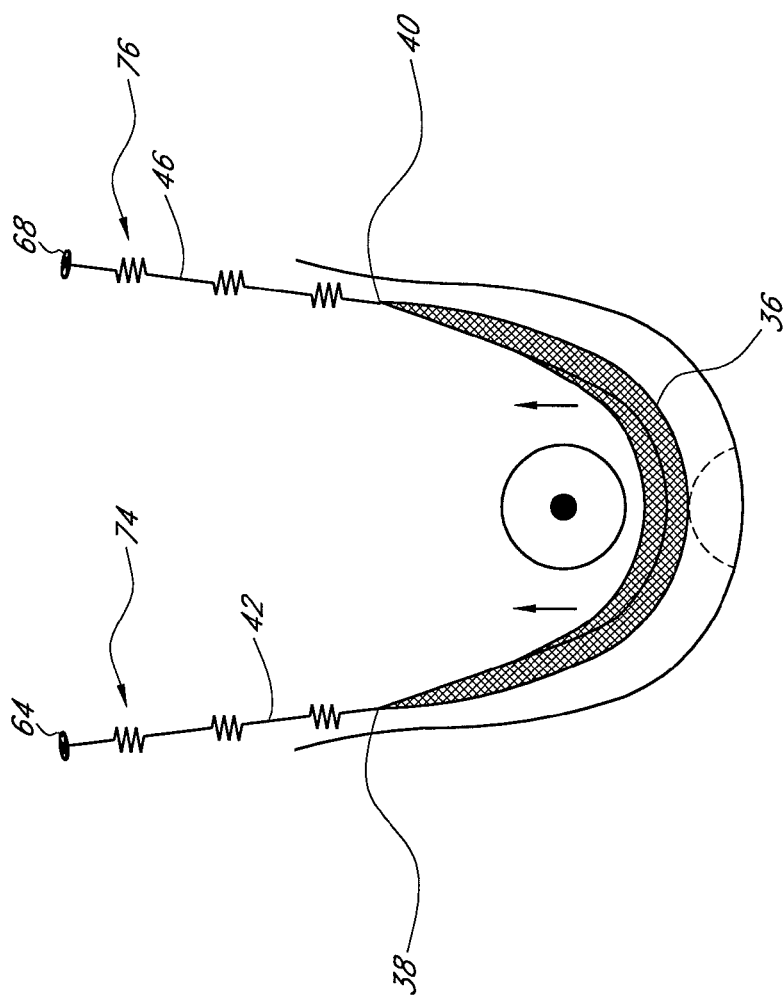

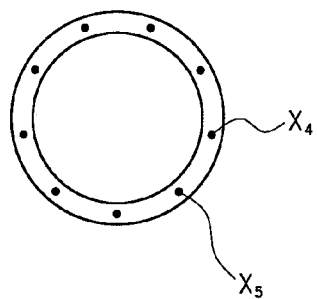
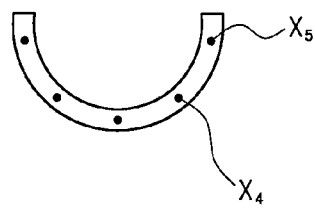
FIG. 7A  FIG. 7B  FIG. 7C
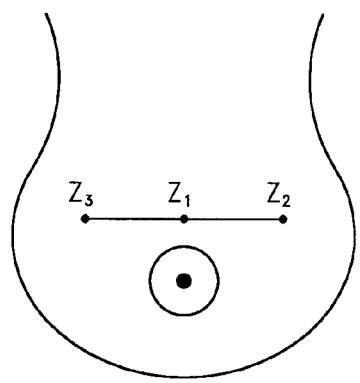
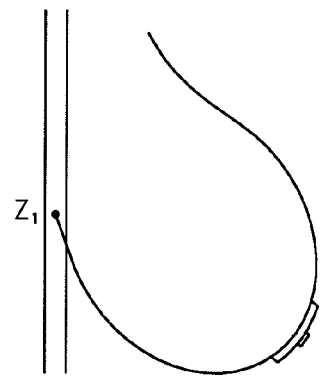
FIG. 8A  FIG. 8B

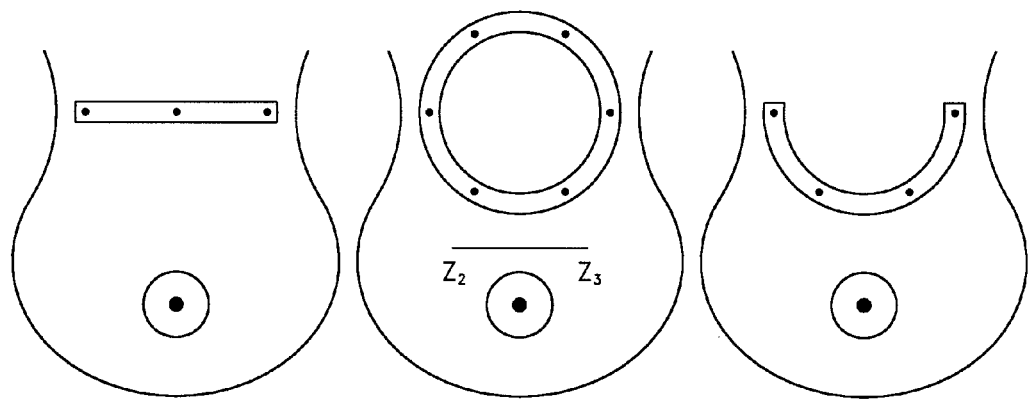
FIG. 11
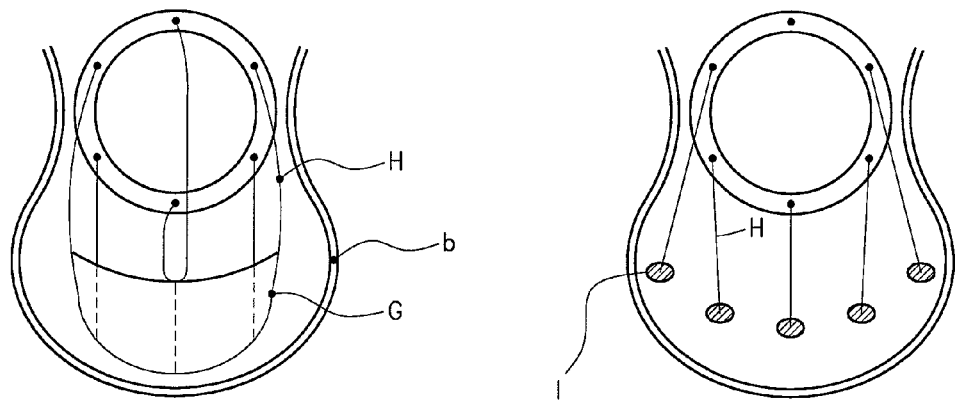
FIG. 12          FIG. 13

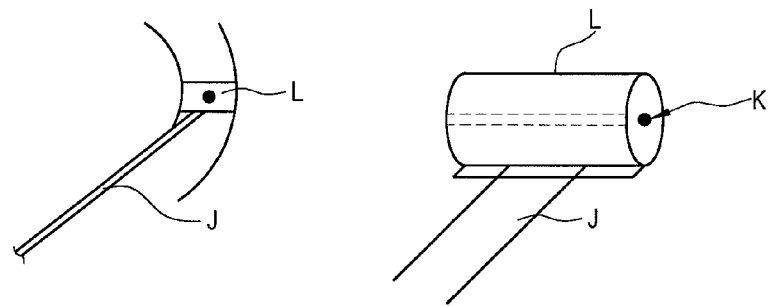
FIG. 14A  FIG. 14B
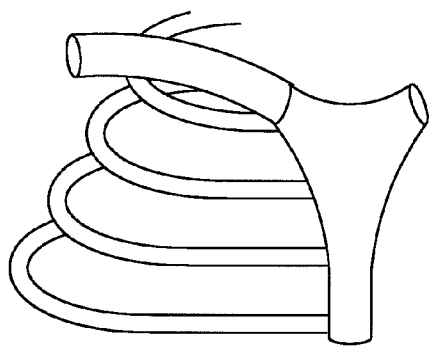
FIG. 15

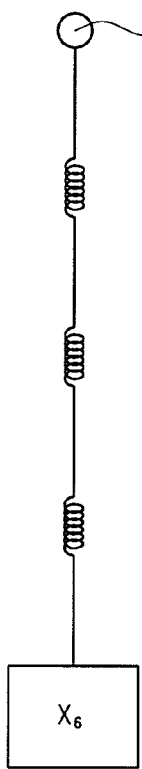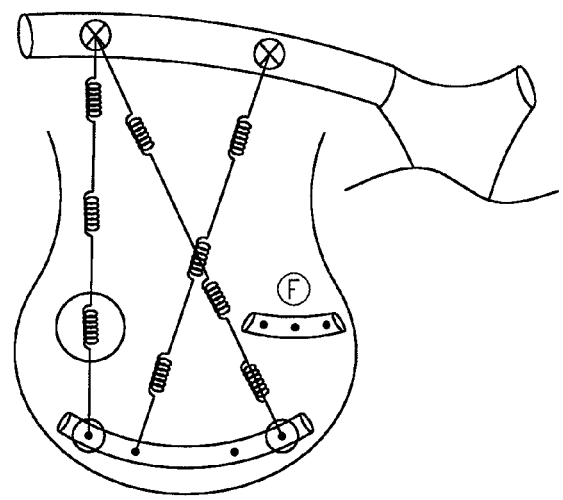
FIG. 19  FIG. 20
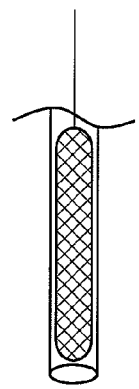
FIG. 21A  FIG. 21B

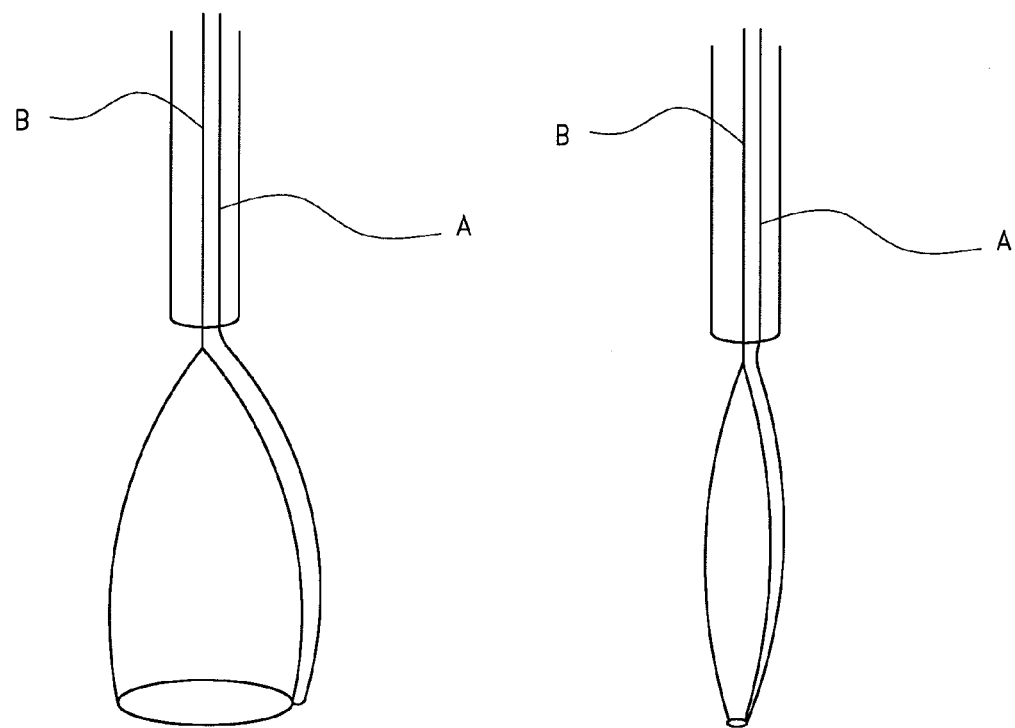
FIG. 22A  FIG. 22B
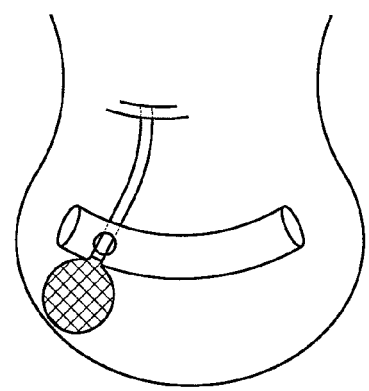
FIG. 23

NONAUGMENTIVE MASTOPEXY

PRIORITY INFORMATION

This application claims priority under 35 U.S.C. §119 to U.S. Provisional Patent Application Ser. No. 60/820,565, filed Jul. 27, 2006, the disclosure of which is incorporated in its entirety herein by reference.

BACKGROUND OF THE INVENTION

1. Field of the Invention

This invention relates to apparatus and methods for mastopexy or "breastlift" procedures and devices, and more particularly to devices and methods for minimally invasive mastopexy which may be accomplished with or without augmentation.

2. Description of the Related Art

Breast augmentation, reduction and reconstructive surgeries have become commonplace within the last twenty years. In a breast augmentation procedure, a breast prosthesis is implanted into the chest to enhance the apparent size of the naturally occurring breast tissue. In a breast reconstructive procedure, a breast prosthetic is used to replace the diseased breast tissue after the diseased breast tissue has been surgically removed.

Breast augmentation procedures and breast reconstructive procedures usually are performed using one of three common surgical techniques. The simplest of the surgical techniques is that used in the "over the muscle" breast augmentation procedure. Using such a technique, a single breast prosthesis is placed between the pectoral muscle in the chest and the mammary glands. In such a procedure, the breast prosthesis is in complete contact with the breast tissue, but is unsupported by any muscle.

A second technique used in breast augmentation surgery is a partial submuscular implant procedure. In this procedure, a breast prosthesis is placed partially under the pectoral muscle through either an incision in the nipple or an inframammary crease incision. During surgery, the muscle support fascia at the bottom of the pectoral muscle is disrupted and the breast prosthesis is partially inserted under the muscle. The result is that the top of the breast prosthesis is covered by the pectoral muscle and the bottom is not. This allows the bottom of the augmented breast to appear round while the top of the chest appears more natural.

A third technique used in breast surgery is the completely under the muscle technique. In this technique, the intra-muscle support fascia of the pectoral muscle is not cut. Rather, the breast prosthesis is placed entirely under the pectoral muscle and is supported by the muscle facia at the bottom.

Another procedure in the evolving field of cosmetic surgery involves mastopexy or "breastlift" surgery. Factors such as pregnancy, nursing, physical activity, time, gravity, and the like may affect skin thickness and tone. As skin loses elasticity, shape and firmness consequently decline over time. Breastlift, or mastopexy, is a surgical procedure to raise and reshape breasts. In conventional mastopexy, bio-compatible implants are often inserted under muscle, or under mammary tissues above muscle in order to alter both firmness and size. Mastopexy in combination with augmentation can be seen, for example, in US patent Publication No. 2006/0036333 A1, to Smith, et al.

Notwithstanding the foregoing developments, however, there remains a need for a minimally invasive system for accomplishing mastopexy to resolve or address ptosis, particularly in patients who do not desire an accompanying augmentation.

SUMMARY OF THE INVENTION

There is provided in accordance with one aspect of the present invention a minimally invasive mastopexy system. The system comprises a soft tissue support sling, and an elongate tubular introducer. The introducer has a proximal end, a distal end and a central lumen for removably receiving the support sling. At least one bone anchor is provided, for anchoring the support sling to bone.

The minimally invasive mastopexy system may additionally comprise a second bone anchor, and either or both bone anchors are provided with a connector for adjustable connection to the sling. The support sling may additionally comprise a proximal support line and a distal support line for suspending the sling from the anchors. The mastopexy system may include at least one strain relief, on the sling or the support lines, for permitting elastic stretching and return of the support sling.

The introducer may be a tunneling sheath, for tunneling through soft tissue. The introducer may be provided with a plurality of apertures through the side wall, and in communication with the central lumen, for infusion of media such as drugs or local anesthesia into adjacent tissue. The system may include a separate tunneling sheath, in addition to the tubular introducer.

In some embodiments, the system may include at least a first and a second soft tissue support sling. The first soft tissue support sling may be a different size than the second soft tissue support sling.

Further features and advantages of the present invention will become apparent from the detailed description of preferred embodiments which follows, when considered together with the attached drawings and claims.

BRIEF DESCRIPTION OF THE DRAWINGS

In FIG. 4A, the tunneling tube is being placed into the axilla. In FIG. 4B, the tube has been advanced around and the steerable needle has been used to access the bony anchor on the medial aspect of the sternum. In FIG. 4C the tube is being gently withdrawn as the leading edge support line is fixed manually to the medial aspect of the sternum and the sling is being deployed in the breast tissue. In FIG. 4D the tunneling from the axillary entry site to the lateral bone anchor of the clavicle has been performed and the tailing edge support line has now been placed through the subcutaneous tissue and attached to the bone anchor.

FIG. 5 demonstrates the sling in place and gives an anterior-posterior view. The support lines are schematically shown with their built in spring constants to help in the dynamic nature of the sling.

FIG. 6 is a lateral view of the assembly shown in FIG. 5, showing the dynamic response of the illustrated embodiment.

FIG. 7A through 7C illustrate different chest wall attachment structures.

FIG. 8A is an anterior-posterior view showing an access incision location.

FIG. 8B is a lateral view of the incision location of FIG. 8A.

FIG. 11 illustrates potential locations on the chest wall for the anchors illustrated in FIGS. 7A through 7C.

FIG. 12 is an anterior-posterior view of the support ring of FIG. 7A, with a first soft tissue suspension structure attached.

FIG. 13 is an anterior-posterior view of the support ring of FIG. 7A, with a second type of soft tissue attachment structure attached.

FIG. 14A is a fragmentary, schematic view of an adjustment structure such as a pulley attached to a support ring.

FIG. 14B is an enlarged view of the pulley of FIG. 14A.

FIG. 15 is a fragmentary schematic representation of the boney anatomy available for attachment.

FIG. 19 schematically illustrates a springy, strain relief function between a boney attachment point $X_5$ and a supported mass $X_6$.

FIG. 20 is an anterior-posterior view of a mastopexy system having strain relief capability.

FIG. 21A is a schematic illustration of a mesh soft tissue anchor in an unconstrained configuration.

FIG. 21B is a schematic illustration of the mesh tissue anchor of FIG. 21A, compressed within a deployment sleeve.

FIGS. 22A and 22B are schematic illustrations of a tissue grabbing anchor, in an open and closed configuration, respectively.

FIG. 23 is an anterior-posterior view of a mastopexy construct in accordance with the present invention.

DETAILED DESCRIPTION OF THE PREFERRED EMBODIMENT

Figure 1:
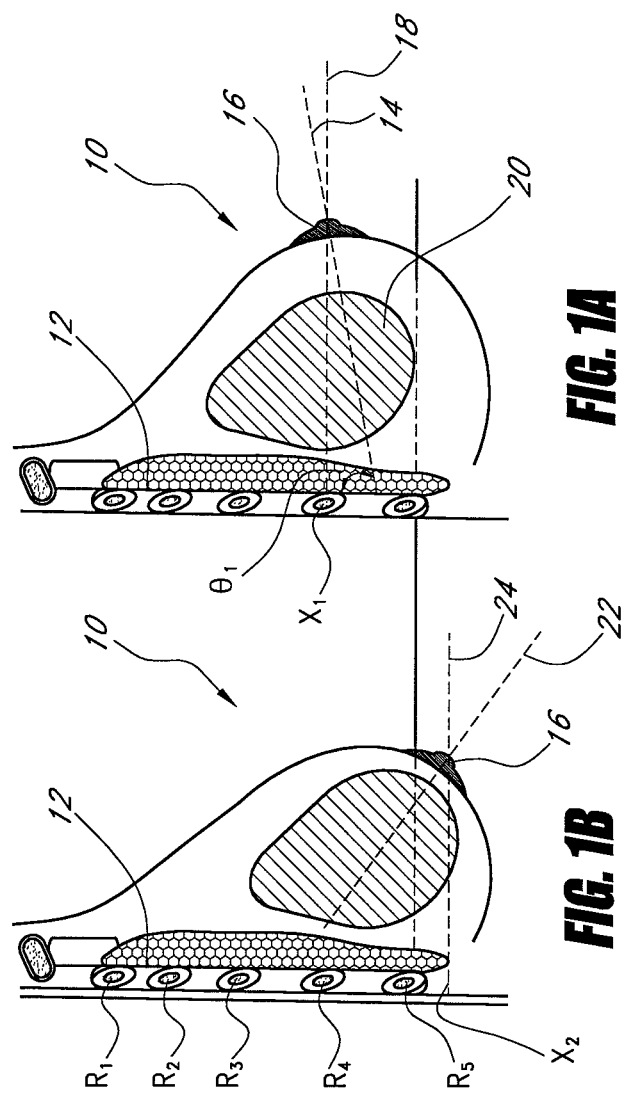
FIG. 1 demonstrates the overall goal of the technique to change a nipple with ptosis (FIG. 1B) to a nipple that points up (FIG. 1A). A reference line drawn orthogonal to the chest wall illustrates superior elevation of the repositioned breast mass in FIG. 1A compared to FIG. 1B.

Surgical techniques for breast reduction and reshaping have not changed significantly over the past generation. As breasts age, the trajectory of the nipple relative to the body axis changes. The pendulous mass of areolar tissue also descends causing a change in nipple line relative to the rib cage.

The present invention provides percutaneous, minimally invasive technologies for tissue reorientation and specifically in connection with mastopexy. This involves elevating the trajectory of the nipple relative to the chest wall, as well as the position of the pendulous on the chest wall. It can also be applied to buttocks lifts or any other type of soft tissue suspension or reorientation. Potential applications include breast ptosis, buttocks ptosis, and gullet suspension. In addition, the implant of the present invention can be positioned to achieve suspension and/or stabilization of the loose connective tissue on the upper arm and more specifically to the soft tissue over the triceps muscle.

Breast ptosis is an interesting phenomenon that occurs when the nipple descends on the chest wall and points downward. This occurs over a period of time in the normal aging process for women with moderate to large breasts; it occurs less so for women with small breasts.

There is also an entity called pseudoptosis where, although the nipple stays above a line drawn orthogonal to the chest wall, the pendulous of the breast sinks below on the chest wall. Mechanisms of the development of breast ptosis involve mainly changes in the anatomy of the breast mass itself as a function of time. Cooper's ligaments, which are a diffuse set of connective tissue that run throughout the breast and cannot be defined anatomically as one specific entity, tend to atrophy and stretch. This causes the pendulous to fall on the chest wall. In addition, the actual tissue within the breast itself, the ducts, the glands that make up a great deal of the tissue changes with time, specifically after adult menopause and this change in the substance of the breast tissue itself causes it to descend on the chest wall.

The likely patient population for nonaugmentive mastopexy in accordance with the present invention includes women ages 35 to 75 with sagging breasts. Nipples would be pointing downward, breast mass descended on the chest wall. The skin remains cosmetically viable and there is no significant dermatomalacia. The likely patients are not interested in implants whether they be silicone or saline and they do not require augmentation and would not consider reduction mammoplasty secondary to scarring.

One implementation of the invention provides a two attachment point adjustable dynamic sling that is minimally invasive during placement. It anchors at two points connected by support lines and may comprise a polymer fabric sling. It is preferably dynamic in that it will not restrict the natural breast motion. With augmentive mastopexy or breast enlargement, the breasts can become so firm that they lose their natural movement. In addition, the implants of the present invention may be adjustable so that over time as the breasts continue to sag, a small adjustment will allow them to be repositioned. This could be accomplished non invasively if a magnet driven winding mechanism could be included in the bone anchors In general, the implant of the present invention achieves two distinct types of tissue reorientation on each patient. One is to relocate the center of the base of the breast mass to a point more superior on the thorax or cranial on the thorax. Another is to redirect the line defined by the erect nipple in relation to the chest wall. Although it would be possible to adjust the trajectory of the nipple to any angle, we would imagine that an acute superior trajectory whether that be midline, medial, or lateral would look best cosmetically.

Techniques for repositioning the breast mass include several different approaches. One is a support ring fixed to the chest wall. Another is a dynamic sling. Polymer tubes can be placed into the breast mass itself that would then be suspended via support lines to bone anchor points, or a Nitinol construct in the form of a mesh would act as a sling. Bony anchor points will vary depending on the size of the breast and the body habitus of the patient, but certainly anchors could be considered along the clavicle, along the medial aspect of the sternum, along any of the ribs on the chest wall, and also the scapula. The curvature of the ribs as they go from anterior to posterior will have to be taken into consideration as running of suspensory cables or bone anchors is accomplished and as different bone anchor locations are chosen.

In accordance with one specific technique of the present invention, a dynamic sling with connecting support lines is anchored from bone and positioned within the breast tissue. The support lines are preferably dynamic such as would be achieved by a Nitinol wire with small springs located at intervals along its length. The Nitinol would be shape memory set into a spring-like configuration with skip areas that were straight. In this way they would have a force constant that would hold the breast up and then when the breast moved and the load increased the springs would be able to stretch and this would give the natural motion back to the breast. Alternative biasing structures are also contemplated. The supporting lines can be made from alloys and metals other than Nitinol.

In accordance with a procedure of the present invention, patients would initially be placed in a supine position. An incision would be made in the vicinity of the axilla. The incision would be no more than approximately 1 cm. A substantially inflexible deployment tube with a stylette would then be advanced into the incision. The breast would be cupped in one hand and the deployment tube would be guided through the breast mass subcutaneously by using manual palpation. The tube in its simplest form would look like a 6 or 7 French guide sheath, possibly 8 French. It would have a round tipped obturator and this would aid in blunt dissection.

Alternatively the deployment tube may comprise a metal, alloy or polymeric composition that was malleable or configured for lateral flexibility, something similar to a tunneling obturator used to tunnel ventriculperitoneal shunt from the cranil end to the abdominal incision. This deployment tube may be guided by bending in situ by manual palpation. The tube is guided around serially from the incision site down, making a turn medially, and then going superiorly up again towards the clavicle. An incision would then be made above the clavicle at the bone anchor site of choice.

For example, one bone anchor point may be at the medial aspect of the breast at the junction of the sternum and the clavicle, either on the clavicle or on the sternum, but normally not in the articulation of these two. A small incision of no more than approximately 1 cm. would be made and blunt dissection accomplished down to the bone. The bone would then be drilled. The drilled bore may be tapped and a threaded bone anchor screwed into place. The top of the bone anchor has an aperture or other connector that would accept a suture or a wire or other corresponding connector on the sling.

Similarly, laterally a bone anchor site is chosen on the clavicle approximately 4 cm. or so above the entry site in the axilla. An incision would be made and a similar bone anchor would be placed. The bone anchors would be exposed so that the clinician could not only palpate the bone anchor, but also under direct visualization see the bone anchor connector where the connecting support lines would have to be placed.

The next step would be to position the implant. The implant may be loaded into the deployment tube that may already be in position. In general, the implant has an elongate body, at least one leading support line and at least one trailing support line. The leading support line may have a leading end comprising a steerable needle which is fed first into the tube. Following the steerable needle would be the leading support line. This would then be connected to the leading end of the implant body. The tailing end of the implant body is provided with one or more support lines, which might also have needles attached to them.

Once the implant is advanced into the tube that was already in position with the tip of the tube in the subcutaneous tissue just inferior to the incision on the clavicle, the leading needle is advanced distally out of the tube where it may be manually grasped and then advanced through the aperture in the bone anchor. The leading and trailing support lines would then be used to position the sling so that it is symmetrically distributed in the breast. The deployment tube would then be proximally retracted and the sling would remain in the breast tissue.

At this point, a first support line extends out of the incision where the medial bone anchor was placed in the clavicle/sternum area and a second support line extends out of the incision in the vicinity of the axilla. The lateral or axillary support line is tunneled from the axilla up to the lateral bone anchor such as by direct vision just by taking the needle on the proximal end of the trailing support line and running it subcutaneously back into the axilla site and then pushing it up towards the medial bone anchor and threading it through the bone anchor connector.

Once both support lines are threaded through the respective bone anchors the patient is moved to a sitting position under general anesthesia so the tension on the support lines can be adjusted to achieve the desired cosmetic result. Then the support lines are locked in place to the anchors by screwing a lock nut into the hole on the bone anchor or otherwise securing the support line to the bone anchor so that it is now firmly secured with respect to the bone.

It is possible to adjust the position of the sling but rather than pulling it through breast tissue, the adjustment of the sling and the positioning of the sling should be done within the tube. Therefore, the delivery tube placement and location within the breast mass will define exactly where the sling winds up relative to the pendulous.

It may be necessary or desirable in some cases to use more than one sling. This could be done by using the same bone anchors more than once, so two or three or more slings are suspended from the same set of bone anchors, or it might be necessary to have bone anchors in multiple areas with multiple slings, trying to deal with redirecting the pendulous.

There are numerous potential sites for each of the medial and lateral bone anchors. The sternal end of the clavicle may be a good site for bone anchors anywhere the mid sternum area. The first rib, lower points on the sternum, or any of a variety of positions on any of the ribs.

Looking at sagittal sections of the chest wall, a glandular mass is suspended off the chest wall. There is a fascia that overlies the pectoralis muscles and the pectoral fascia provides an avascular plane between the breast itself and the chest wall. The clavicle appears to come to the surface under more fatty subcutaneous tissue and then inferior to the clavicle starts the pectoralis muscles. The ribs are below the pectoralis muscle and, therefore, in order to advance to the second rib, the third rib, etc., it would be necessary to go through the pectoralis muscle. Preferably, bone anchors are driven into the center of the rib and away from the inferior aspect of the rib where the nerve, artery, and vein bundles run.

Supraclavicular nerves will need to be considered when doing the dissections and, in addition, the cephalic vein is in the region of the clavicle as well as the venous plexus overlying the belly of the hyoid 17, which might send venous structures down towards the medial sternum that could thwart attempts at placement of bone anchors.

Referring to FIGS. 1A and 1B, the above-mentioned changes resulting in ptosis can be described in a more objective manner. A cross section of a breast 10 is shown schematically in relation to chest wall 12. A reference line 14 extends along an axis defined by the nipple 16 and is projected back to the chest wall 12. The angle of incidence θ is one method for defining nipple trajectory. In FIG. 1A, the picture depicts a young breast prior to change in nipple trajectory. The reference line 18 in FIG. 1A, is drawn between the nipple and the chest wall and defines the intercostal level $X_1$ that corresponds to the nipple position relative to the chest wall. The round crosshatched area 20 in FIG. 1A defines the pendulous of the breast mass, the position of which can be noted relative to the intercostal level $X_1$ and relative to reference line 18.

In FIG. 1B, an aged breast is depicted. Note the reference line 22 defining nipple trajectory forming angle $θ_2$ with the chest wall defines a vector distinctly different from reference line 14 in FIG. 1A. In fact, line 22 is inclined down and line 14 is inclined up. The line 24 in FIG. 1B drawn as a perpendicular between the nipple and the chest wall is incident on the chest wall at an intercostal level $X_2$ well below that depicted as $X_1$ in FIG. 1A. The intercostal distance $X_1X_2$ can vary by more than one intercostal level, and helps define the inferior migration of the breast pendulous mass over time.

Present surgical techniques of mammoplasty seek to transform FIG. 1B into FIG. 1A by a variety of techniques. All surgical techniques rely on breast mass reduction and surgical nipple excision and reimplantation at a higher intercostal level. This results in disfiguring scars and in some cases, complete denervation of the nipple. Although nipple trajectory and the position of the pendulous relative to the chest wall are corrected, unsightly scars and desensitization of the nipple may result as unwanted side effects of the cosmetic correction.

One embodiment of a device in accordance with the present invention for percutaneous minimally invasive manipulation of nipple trajectory and position of the pendulous mass relative to the chest wall will be discussed below.

Figure 2:
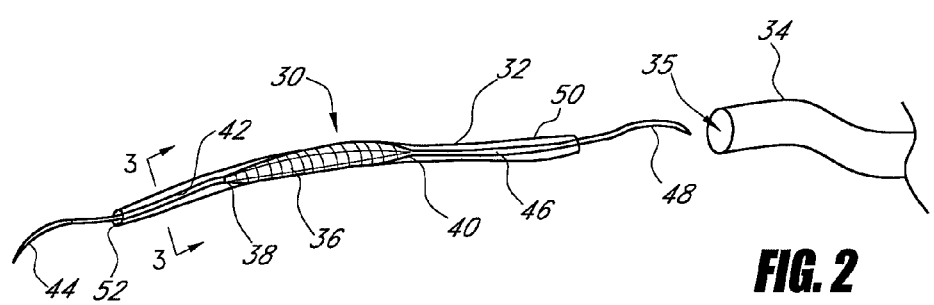
FIG. 2 is a side elevational, schematic view of an implant assembly in accordance with one embodiment of the present invention.

Referring to FIG. 2, there is illustrated an implant assembly in accordance with one aspect of the present invention. The implant 30 is illustrated as positioned within an implant sleeve 32, the combination of which may be positioned within an outer tunneling sheath 34 as has been discussed.

In general, the implant 30 comprises a basket or sling portion 36 extending between a proximal end 38 and a distal end 40. The basket 36 may comprise any of a variety of configurations, depending upon the desired clinical performance. In general, basket 36 comprises a polymeric or wire mesh, such as a woven or non-woven fabric, or a plurality of axially extending filaments, which may be connected by transversely extending filaments. The basket 36 may be expandable from a reduced cross sectional configuration for fitting within the implant sleeve 32 during delivery, and an expanded cross sectional configuration for providing tissue support post implantation. In the reduced, delivery configuration, the basket 36 will preferably fit within an implant sleeve 32 having an inside diameter of no greater than about 0.5 inches, preferably no greater than about 0.25 inches and optimally, no greater than about 0.125 inches. In the transversely expanded configuration, the basket 36 may have a maximum transverse dimension of at least about 0.5 inches, in some embodiments at least about 0.75 inches, and, depending upon the desired clinical performance, at least about 1 inch or greater.

The implant 30 may be provided in graduated sizes, individually or in kits, to allow selection based upon clinical judgment in an individual implantation. For example, in some implantations, two or three or four or more relatively small implants 30 may be desired. In an alternate implementation of the invention, one or two or three larger implants 30 may be desired as an alternative. The selection of a particular size and number of implants 30 to be utilized in a particular procedure is a matter of clinical judgment, taking into account the desired cosmetic result as well as extent of lateral dissection and other procedural aspects that may be more or less desirable for a particular patient.

The basket 36 may comprise any of a variety of biocompatible, flexible, implantable materials as are known in the medical device arts. For example, any of a variety of suture materials such as polyethylene may be used. Implantable polymers such as PEBAX, PEEK, nylon, PET, ePTFE, PTFE and the like may also be used. Elastic materials such as silicone or latex may also be used. Alternatively, metal wire or a laser cut metal lattice may be utilized. Suitable metals may include stainless steel, titanium, and a variety of shape memory metals such as alloys of nickel and titanium (e.g., Nitinol)

The proximal end 38 of basket 36 is attached to a proximal support line 42. Proximal support line 42 extends between the basket 36 and a proximal end of the implant, and may be provided with a proximal needle 44. Proximal needle 44 may be convenient for facilitating tunneling of the proximal support line 42 from the percutaneous access point in the axilla, to a lateral bone anchor as has been discussed.

The distal end 40 of basket 36 is provided with a distal support line 46 which may also be provided with a distal needle 48. Distal needle 48 may conveniently facilitate advance of the distal support line 46 in the direction of the medial bone anchor as has been discussed.

The dimensions of the implant 30 may be varied considerably, depending upon the desired cosmetic result. In general, the basket 36 may have a length within the range of from about 1 inch to about 8 inches, and, in many embodiments, will be within the range of from about 2 inches to about 6 inches. Alternatively, the basket 36 can extend the entire length of the implant, such as from proximal needle 44 to distal needle 48 if proximal needle 44 and distal needle 48 are initially included on the implant 30. Proximal support line 42 and distal support line 46, when provided, may have an axial length of at least about 4 inches each, and, often at least about 8 inches or 12 inches each. The length of the implant 30 overall, including the proximal support line 42 and distal support line 46 should be sufficiently long to accommodate most patients, as well as have sufficient excess support line length to facilitate balancing the location of the implant 30 and securing the implant 30 to the bone anchors as will be appreciated by those of skill in the art in view of the disclosure herein. The needles 44 and 48, and excess support line will be severed and discarded following locking of the implant to the bone anchors.

The implant 30 is illustrated as positioned within an implant sleeve 32. Implant sleeve 32 comprises an elongate flexible tubular body 50, having a central lumen 52 for slidably receiving the implant 30. Although the use of an implant sleeve 32 is optional, it may be desirable for maintaining the basket 36 in a reduced crossing profile configuration for implantation and positioning of the implant 30. Tubular body 50 may comprise any of a variety of polymeric materials known in the catheter arts, such as those polymers identified above. Tubular body 50 may be formed by known extrusion techniques. Preferably, the tubular body 50 will have an axial length sufficient to enclose the basket 36 and will normally be at least about 2 inches long, often at least about 6 inches long, and, in many embodiments, at least about 12 inches long.

The tubular body 50 may be provided with a plurality of sidewall apertures along its length, for communicating between the central lumen 52 and the outside of the implant sleeve 32. In this embodiment, the proximal end of the tubular body 50 may be placed in fluid communication with a source of infusion media. In this construction, if the implant sleeve 32 is utilized to position the implant 30 in the absence of a separate outer tunneling sheath 34, suitable media such as lidocaine with epinephrine may be infused through the central lumen 52 and out of the side apertures on a periodic or continuous basis to infiltrate the adjacent tissue throughout the procedure. In an embodiment of the invention in which the implant sleeve 32 and/or implant 30 subassembly is advanced though a separate outer tunneling sheath 34, the outer tunneling sheath 34 may be provided with a plurality of apertures in communication with a central lumen 35, to similarly permit infiltration of adjacent tissue with media such as lidocaine and epinephrine.

Figure 3:
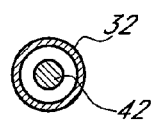
FIG. 3 is a cross sectional view taken along the line 3-3.
Figure 4A:
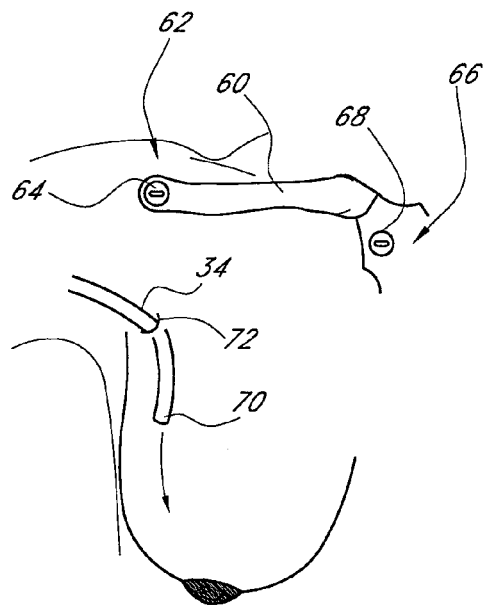
FIGS. 4A-D demonstrate the technique of in situ bending of the malleable tunneling tube as it is gently guided through the breast tissue forming almost a u-shape to get from its insertion site in the axilla into the medial aspect of the clavicle or even to the sternum through the subcutaneous tissue.

An implantation sequence for the device illustrated in FIGS. 2 and 3 may be understood by reference to FIGS. 4A-4D. Referring to FIG. 4A, a clavical 60 is illustrated schematically, as a reference for the location of the bone anchors. As will be appreciated by those of skill in the art in view of the disclosure herein, the bone anchors may be secured to any of a wide variety of locations and the examples provided herein are merely illustrative of one particular implementation of the invention. In addition, attachment structures other than bone anchors may be utilized, such as by looping support lines entirely around a bone, or attachment of support lines to soft tissue utilizing any of a variety of hooks, barbs, staples sutures, tissue ingrowth structures, soft tissue anchors and the like. Bone anchors are preferably preferred, due to their perceived durability.

Any of a variety of bone anchors may be utilized in the practice of the present invention. In general, the bone anchors will include a bone engaging portion which may be a threaded shaft, or a shaft with teeth or other textured surface, for wedging into a predrilled bore in the bone. Alternatively, bone anchors employing an axially extending shaft with laterally advanceable wings or lever arms such as for deployment in the cancellous bone may also be utilized.

Bone anchors will additionally include a connector, such an eyelet for connection of a suture or other support line. The eyelet is preferably changeable from a first configuration in which the suture or other support line may be freely advanced axially therethrough, such as for initial connection of the support line to the anchor as well as for permitting adjustment of the location of the implant prior to locking the implant to the bone anchor. A variety of bone anchors are known in the art, which accommodate adjustment between a locked and an unlocked configuration, through the use of a variety of structures such as compression screws, cam surfaces, interference engagement surfaces, and the like.

Referring to FIG. 4A, a first bone anchor 64 is illustrated in position at a first attachment site 62 on the clavical 60. A second bone anchor 68 is illustrated at a second attachment site 66, on the sternum.

Although the present illustration shows the bone anchors in position prior to introduction of the implant, the sequence of steps can be modified. Accordingly, the implant can be positioned prior to installation of the bone anchors, or in between installation of a first of the bone anchors and a second of the bone anchors, depending upon clinical choice.

The distal end 70 of the outer tunneling sheath 34 is illustrated in FIG. 4A as having been introduced through a percutaneous access site 72. The outer tunneling sheath 34 is advanced distally through the access site 72, and manipulated by manual palpation from the access site 72 inferiorly, making a medial turn, and then inclining superiorly towards the clavical. Navigation may be accomplished using a combination of manipulating the tissue orientation, as well as bending or steering the outer tunneling sheath 34 by manual palpation through tissue.

For the advancing step, the outer tunneling sheath 34 may be provided with a distal tip, such as a blunt dissection obturator tip (not shown) or a tissue cutting tip that may be utilized to dissect a pathway through tissue. The obturator tip or dissection tip may be proximally axially retracted from the outer tunneling sheath 34 once the distal end 70 is at a desired location such as that illustrated in FIG. 4B. At that time, the assembly of the implant 30 and implant sleeve 32 may be advanced distally through the outer tunneling sheath 34.

Figure 4B:
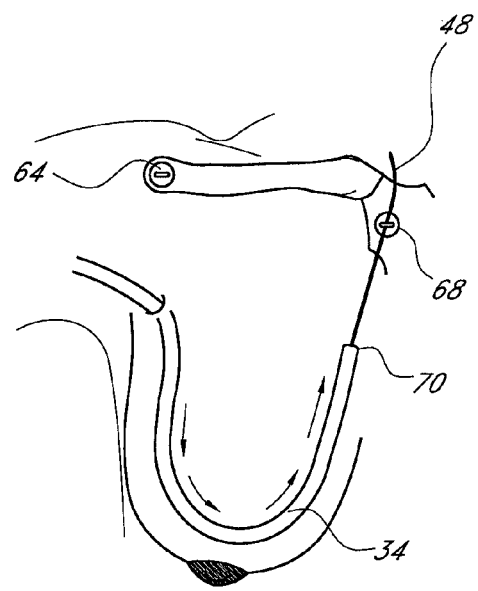

Referring to FIG. 4B, the distal needle 48 has been advanced from the distal end 70 of the outer tunneling sheath 34. At this point, the anchor 68 may be under direct visualization through the anchor access tract, thus permitting direct visualization as the needle 48 is advanced through the aperture or other interlocking structure on the bone anchor 68. Needle 48 is thereafter retracted from the bone anchor 68 to remove slack in the distal support line 46 and also advance the basket 36 into approximately the desired position within the outer tunneling sheath 34.

Figure 4C:
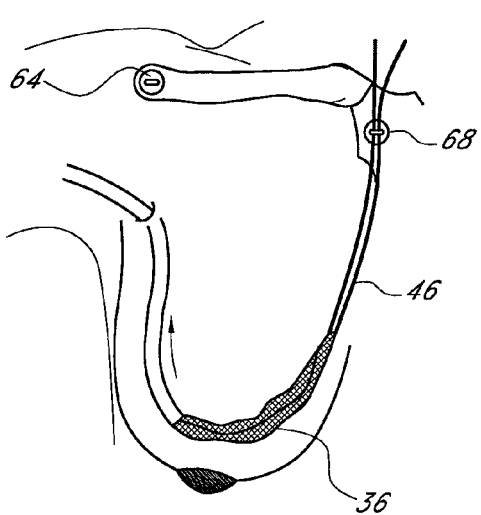
Figure 4D:
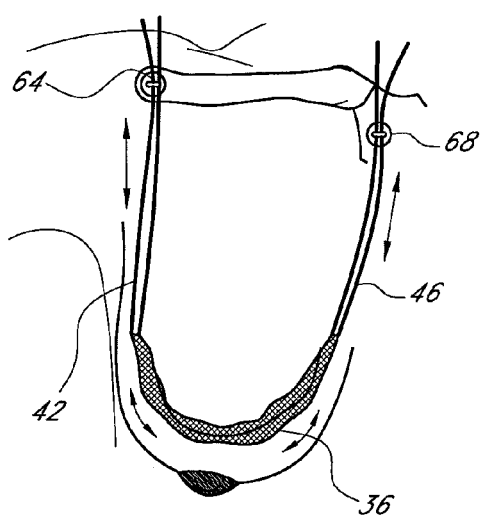

Referring to FIG. 4C, the outer tunneling sheath 34 may be proximally retracted and removed from the patient. The implant sleeve 32 may be left in place over the basket 36, or may also be retracted, exposing the basket 36 to tissue. The distal support line 46 is clamped or held by a clinician, to prevent it from escaping from the anchor 68, which has not yet been locked down on the distal support line 46. For this purpose, the connector on the bone anchor may be provided with a reversible lock, to allow temporary lock down on the support line and release to allow final adjustment before permanent lock down. Alternatively, the implant may be packaged in a kit along with one or two temporary adjustable lock down devices which can be removed and discarded following final adjustment and locking of the support lines.

Following removal of outer tunneling sheath 34, the proximal support line 42 will exit the patient at access site 72. The proximal needle 44 may be thereafter be advanced back through the access site 72, and tunneled subcutaneously in the direction of the lateral anchor 64. The tissue tract which was formed for the implantation of lateral anchor 64 may be utilized for direct visualization as the proximal needle 44 is advanced through the locking aperture on anchor 64, to produce the configuration schematically illustrated in FIG. 4D.

At this point, the proximal support line 42 and distal support line 46 may be placed alternately under tension, to advance the basket 36 back and forth along the tissue tract, until the desired positioned is reached. For this adjustment step, it may be desirable for the implant sleeve 32 to still cover the basket 36, to minimize tissue trauma. For this purpose, the implant sleeve 32 may be provided with an axially elongated indentation, perforation, or other modification to the wall of tubular body 50, to permit the implant sleeve 32 to be split and peeled away from the proximal support line 42 as will be appreciated by those of skill in the art. When configured as a peel away sheath, the implant sleeve 32 may be provided with a pull tab or other handle at its proximal end, preferably centered approximately 180° apart from the perforation line, indent or other modification to facilitate tearing of the implant sleeve 32. In this configuration, the basket 36 may be moved until it has reached a desired location. The bone anchors 64 and 68 may be advanced from an unlocked to a locked configuration, and the excess length of the proximal support line 42 and distal support line 46 may be severed at about the respective bone anchor. The tissue tracts formed for the implantation of the two bone anchors and for access by the outer tunneling sheath 34 may thereafter be closed in accordance with standard techniques.

Although the procedure described above involved implantation of a single implant 30, two or three or four or more implants 30 may also be implanted, as has been discussed. Each implant may be tunneled through a unique tissue tract, and be attached to either the same bone anchors 64 and 68 as have been discussed, or to one or two or three or four or more bone anchors, positioned elsewhere on the clavical, ribs or sternum. The desirability of including more than one implant 30 is a matter of clinical choice, taking into account the patient and the desired result.

The result of various factors such as tissue elasticity and momentum causes normal tissue to respond in a relatively predictable manner, to movement by the patient. Depending upon the desired clinical result, it may be desirable to modify the implant described above to increase the potential range of inferior superior axis motion. This may be accomplished in a variety of ways, one of which is illustrated schematically in FIG. 5.

Referring to FIG. 5, a sling 36 is illustrated in position and secured by a proximal support line 42 to a lateral anchor 64, and by a distal support line 46 to a medial anchor 68. At least a first strain relief 74 is provided in communication with the proximal support wire 42, and at least a second strain relief 76 is provided in communication with the distal support line 46. As used herein, strain relief refers to a structure or a material which permits temporary elongation of the effective axial length of the support line, in response to an increase in load, and returns to an original elongation following removal of the load. Thus, strain relief 74 and 76 may in their simplest form, comprise a spring, or at least a section of elastic material, which can be elongated under load and will return to its original configuration following removal of the load.

The proximal support line 42 may be provided with one or two or three or four or more discrete strain relief 74, or the entire length of the support line 42 may function as a strain relief, such as by construction from a helical spring, or an elastically deformable material. The same configurations can be utilized for the distal support line 46. Alternatively, the strain relief 74 and 76 may be constructed as a part of or attached to the bone anchors 64 and 68. As a further alternative, the sling 36 may be constructed of a material and/or using a weave pattern that permits elastic deformation under load. For example, sling 36 may comprise a plurality of generally parallel extending filaments which connect for example at each of the end points 38 and 40 of the basket 36. Each filament may comprise a zig-zag construction, or a helical construction, or comprise an elastic material, such that is may be elongated under load but not deformed beyond its elastic limit.

The performance of the implant 30 incorporating one or more stain relief constructions 74 and 76 can be seen schematically with respect to FIG. 6. The strain relief 74 and 76 create a bias to return in the direction 80 which is generally superior, with a posterior inclination. The normal reference line 82 may be temporarily changed such as 284 under significant loading, but will return to 82 under the influence of the elastic force generated in the direction 80.

In accordance with alternative implementations of the invention, an anchor is positioned on the pectoralis fascia on the chest wall beneath the breast mass. One example or corollary to this is the underwire of a bra. The underwire can be semicircular or a full circle. It can be malleable or rigid depending upon the support required. A few embodiments of the support ring are pictured in FIGS. 7A-7C.

In FIG. 7A, a fall ring is depicted, in FIG. 7B a semicircular or arc ring is pictured. Note the attachment points to the chest wall $X_4$, $X_5$. A straight support is seen in FIG. 7C.

The material properties of these constraints in FIG. 7 preferably permit delivery to the chest wall through a tube at appropriate diameter.

In one embodiment, an incision is made in the skin beneath the pendulous of the breast mass in the midline, $Z_1$ (FIG. 8) large enough to accept the delivery tube. The incision is defined by the line $Z_2Z_3$ in FIG. 8A. The breast mass must now be dissected in a blunt fashion from the pectoralis fascia, at the level where the support ring in FIG. 7 is to be placed. The desired intercostal level can be identified using varying forms of imaging before or during the procedure. In one embodiment, a blunt dissecting tool is the used, delivered through the aforementioned tube (FIG. 9).

Figure 9:
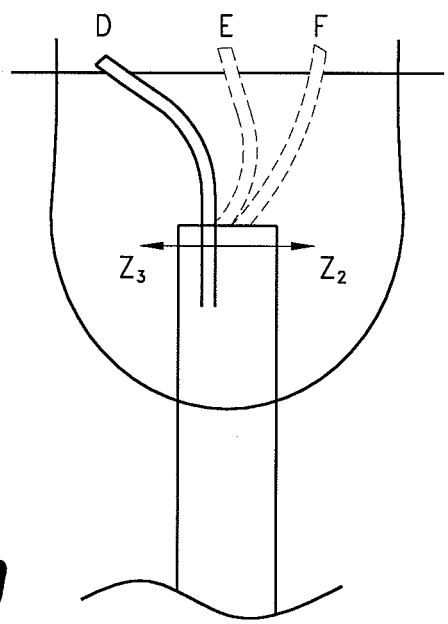
FIG. 9 is a schematic illustration of a blunt dissector tool positioned within the incision 8A.

The blunt dissector in FIG. 9 can be moved in a plane coincident with the chest wall through positions D, E, F in FIG. 9, or any other positions, as a means of clearing the fascia of the pectoralis muscle. The ring or support structure (FIG. 7) is delivered, though the tube in FIG. 9 after the blunt dissector FIG. 9, has been removed.

Figure 10:
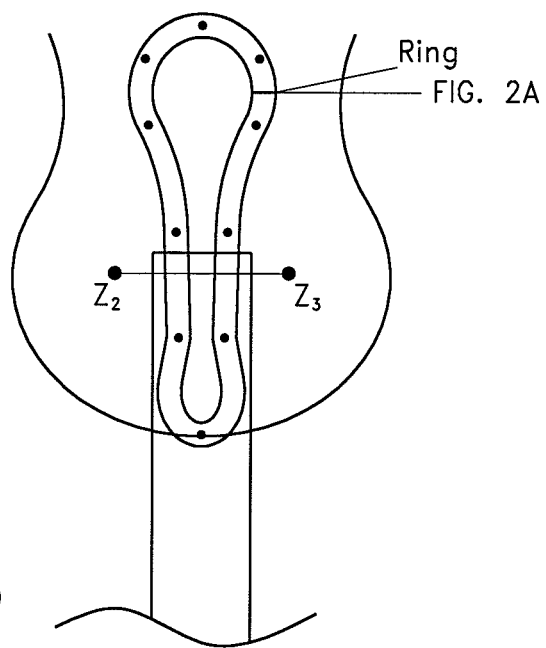
FIG. 10 illustrates deployment of the anchoring ring illustrated in FIG. 7A.

In FIG. 10, the ring depicted in FIG. 7A has been placed inside the delivery tube and is partially delivered onto the surface of the pectoralis fascia. As the ring leaves the tube, it opens. The blunt dissection described in FIG. 9 facilitates the rings positioning and delivery. Once the ring has been delivered (FIG. 11), it will need to be affixed to the chest wall. This can be done using suture, staples, clips, screws or wire, or any other type of fastener.

Each point of fixation of the support structure to the fascia of pectoralis muscle serves a dual function. It holds the ring to the chest wall as well as providing a point of attachment for support devices that will hold the pendulous of the breast mass.

Percutaneous Minimal Mammoplasty

Methods of suspending the pendulous of the breast to the support ring or bar as seen in FIG. 7. Two concepts may be discussed. Method of tethering the suspension and fixation to the loose areola tissue of the pendulous. In one embodiment, a sheet can be placed subcutaneously around the breast without denervating the nipple. In the figure below (FIG. 12), a polymer sheet (G) acts as a parachute with the cords of the chute attached to the suspension ring.

In another embodiment, the polymer sheet could be replaced with polymer discs (I) that are embedded into the areola tissue, each acting as an independent suspension system as a separate point source. (FIG. 13).

Suspension Adjustment

The natural process of aging that lead to change in nipple trajectory and the descended position of the pendulous mass does not slow down or change. As a result, the suspension cords in FIG. 12 and 13 may need to be tightened. Therefore, the need for a non-invasive method to increase tension and decrease length of these parachute cords (FIGS. 12 and 13 and other embodiments previously discussed) may be established. The need to perform this process without invasion, needle puncture, or open incision is preferable for obtaining a sustainable cosmetic result that maximizes patient satisfaction. In one embodiment, a pulley is used at the attachment part on the support ring. (FIG. 14).

In FIG. 14B, a magnified view of the pulley is depicted the suspension cord J, feeds into a spool K, contained within the housing L. The motor for the pulley is activated by an externally applied magnetic field. As a result, adjustments can be made in the awake patient, post operatively without sedation at any time.

Anchoring

The clavicle superiorly, the sternum medially and ribs at any level can act as bone anchor points of fixation for any of the embodiments herein. Given that the nipple is preferably redirected in a three-dimensional space, therefore, an anterior-posterior, cranial-caudial, and medial-lateral degree of adjustment is preferably accomplished. Redirection of the nipple trajectory, repositioning of the pendulous relative to the chest wall is preferably accomplished without cosmetic deformity of the skin surface or dimpling of the nipple. To this end, multiple fixation points with tissue anchors in the areola tissue (or pendulous) may be required.

Referring to FIG. 15 the bony anatomy available for attachment includes the First rib, Clavicle, and Manubrium of the sternum (superior medial).

The first rib and the clavicle define the best and most accessible bony anchor points for superior fixation. These structures are readily palpable through the soft tissue that overlays them, even in obese patients. Although vascular and peripheral nervous system tissue lies proximate to these bony structures, the posterior nature of these structures and bone density makes them ideal fluoroscopic landmarks for percutaneous placement of bone anchors.

The articulation of the clavicle, first rib with the sternum and the anatomic structure known as the manubrium of the sternum provides a superior medial fixation point for a bony anchor. This point would lend a superior medial change in trajectory to the nipple.

Figure 16:
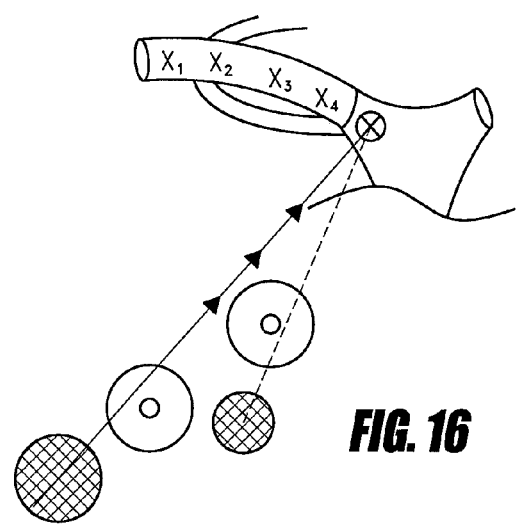
FIG. 16 illustrates the boney anatomy of FIG. 15, and a plurality of potential attachment points along the clavical, for achieving different support vectors.

One could easily envision bony anchor points at points $X_1 \rightarrow X_n$ along the clavicle in FIG. 16 and subsequent vectors that would result in associated change in nipple trajectory associated with the positions of the soft tissue anchors.

Soft Tissue Anchors:

The properties of soft tissue anchors vary depending upon their location and function. A first type of anchor is for the areolar tissue (breast pendulous). Other tissue anchor locations will be considered separately. They include the pectoralis muscle, and facial planes that invest rib and chest wall structures.

Areolar (Pendulous Anchors)

Areolar tissue is unique relative to other tissues in the body. It is in essence fatty tissue that has an increased amount of connective tissue, enervation, as well as ducts. This extra structure lends an increase of overall structure and compliance as well as increases tear out force, relative to pure fatty tissue, yet it certainly is less than muscle or fascia in terms of strength.

The tissue anchor may be placed percutaneously and at one end be attached to the bony anchor at the proximate end. The distal end of the tissue anchor would be embedded into breast tissue in one embodiment of the device (FIG. 13).

Figure 17:
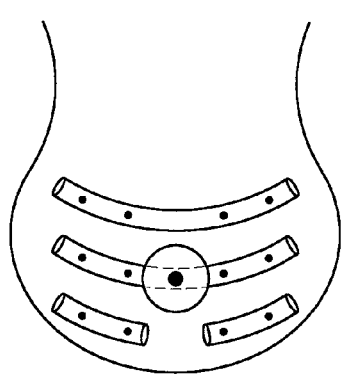
FIG. 17 is an anterior-posterior view illustrating a type of soft tissue anchor.

Another embodiment at the distal end of the tissue anchor embeds into a polymer sheet that cups the breast as in FIG. 12. A third embodiment of the distal tissue anchor is as follows. A hollow polymer tube or two or three or more tubes are inserted into the pendulous of the breast. This tube has attachment sites for the distal end of the tissue anchor as below. These tubes could be easily placed using percutaneous punctures in the pendulous of the breast. They would need resistance to pull through. They could be affixed to the areolar tissue (if needed) using biological glue or suture, electrocautery device or other. (FIG. 17). Any bony fixation point could be connected to any point along a tube as in FIG. 18.

Figure 18:
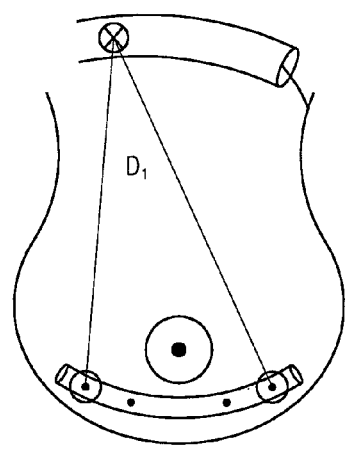
FIG. 18 is an anterior-posterior view illustrating a further support system.

The support cable or wire ($D_1$) in FIG. 18 would be placed percutaneously in a manner similar to threading a retention suture through any large tissue mass, entry point near bony anchor subcutaneous path through breast tissue and distal end threaded into attachment sites in the polymer (or alloy) tube, the need the through skin and the cable is tensioned and cut so the cable would recess subcutaneously.

Cables:

The connections between bony and tissue anchors need to provide support for change in nipple trajectory as well a prevent pull through. They may not be rigid structures but could be. One embodiment of the device would have the property of strain relief in the cables so that if an activity like jumping were to be encountered after implantation, the breast (unconstrained externally) could move up and down naturally without fear of the device pulling through.

In one embodiment, the cables are made from Nitinol wires with springs of varying length, size and force constant (K) that act as strain relief gauges. The spring segment of the cable is firm enough to provide support but can stretch when leading by, for instance, jumping motion.

$X_5$ (FIG. 19) is the bony attachment point (proximal) and $X_6$ is the tissue anchor point (distal). The representation of this type of system can be seen in the figure that follows. In FIG. 20, the anatomic configuration is continued from previous diagrams. The tissue anchor labeled F is smaller in size and eccentrically positioned to depict the fact that tissue anchors can be placed anywhere in the breast tissue.

In another embodiment, the tissue anchor is not a polymer or alloy tube but rather a mesh basket that is constrainable into a percutaneous delivery tube as initially depicted in FIG. 16. The mesh basket or teardrop or ellipse or spherical shape would be porous and allow tissue invagination and scar tissue anchor on an acute subacute and chronic basis.

In FIG. 21A, an elliptical basket made of Nitinol mesh is pictured, in an unconstrained configuration. In FIG. 21B, the same distal tissue anchor is constrained within a tube undeployed. One could envision this tube being used as a percutaneous conduit to connect the proximate end of the cable to the final position of the tissue anchor. The anchor could be filled with bioglue or adhesive by either percutaneous stick or if the connector tube (cable) was hollow, then by direct injection. The size and shape of the tissue anchor would be proportional to the intended position in the breast tissue and the size and shape of the pendulous. In addition, in one embodiment, the size and shape of the tissue anchor is variable and can be adjusted in situ.

In one embodiment, the tissue anchor would be placed in an open configuration, grab tissue, and then close around the tissue to grab and incorporate it within the mesh as in FIG. 22. In FIG. 22A, the device or distal tissue anchor is in an open configuration, the distal end of the device is like a lasso and wire labeled A is used to close the distal loop and act to grab tissue. Although not pictured, the basket is porous either as a mesh or solid perforated sheet. In another embodiment, the polymer or alloy tubes are perforated and the method of attachment is performed by threading a tube from the bone anchor to the polymer tube and delivering or expanding the mesh device distal to the perforated portion in the polymer tube, as below.

Figure 24A:
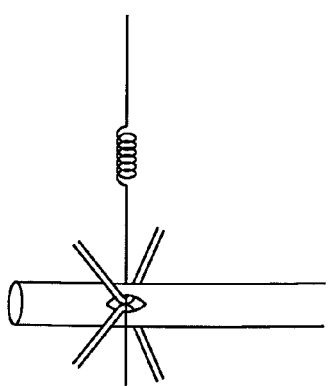
FIG. 24A illustrates a multifilament anchor attached to a support tube.
Figure 24B:
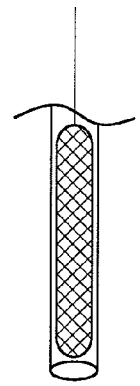
FIG. 24B illustrates the multifilament anchor of FIG. 24A, constrained within a delivery tube.
Figure 24C:
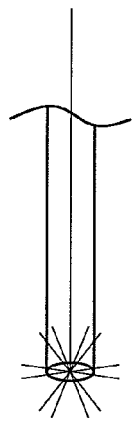
FIG. 24C illustrates the multifilament anchor of FIG. 24A and 24B, deployed within soft tissue.

In an additional embodiment, the connective tissue, distal cable and the polymer tube is connected by passing a coaxial system through the polymer tube hole and deploying a cable with supra structure at its distal end as pictured in FIG. 24. This structure serves to act as an attachment or pull through point to the polymer tube while additionally acting as a tissue anchor distal to the polymer tube.

In FIG. 24A, the distal end of the cable has been inserted through the hole in the polymer support tube and a plurality of wires at its distal end are unsheathed as a means of securing the tube and acting as unsheathed tissue anchor. In 24B, the plurality of wires are constrained within the delivery tube. In 24C, the delivery tube remains in place with the plurality of wires deployed.

Desirable properties of the device include 1) Percutaneous placement. 2) Image guided, fluoroscopy drive, also could consider ultrasound—possibly adjustments in office or surgery center. 3) Strain relief on the support lines and/or sling attached to anchors so that normal motion of breast undisturbed. 4) Adjustable—either minor outpatient procedure or external magnet or electrical signal drives cable reel near bone anchors. 5) Implant does not change texture or feel of the breast to manual palpation. 6) Cannot interfere with mammography images 7) MRI compatible. 8) Minimal tissue dissection required for placement and stabilization. 9) Tissue anchor insertion cannot interfere with nipple sensation or lactation. 10) Patient should be able to jump on a trampoline without "fear of device" damage, and with natural motion of the breast tissue.

What is claimed is:

1. A method of supporting tissue of a breast, comprising the steps of:
   introducing a flexible support to a position between the chest wall and the breast mass;
   introducing at least a first and a second soft tissue anchors into breast tissue beneath the support;
   suspending the first soft tissue anchor from a first location on the support with a first generally linear suspension element to support the breast mass, and
   suspending the second soft tissue anchor from a second location on the support with a second generally linear suspension element to support the breast mass,
   wherein after the suspending steps the first soft tissue anchor is suspended solely by the first suspension element beneath the support and the first suspension element and the second soft tissue anchor is suspended solely by the second suspension element beneath the support and the second suspension element.

2. The method of claim 1, wherein the support comprises a curved segment from a first end of the support to a second end of the support.
3. The method of claim 1, wherein the support comprises a generally linear configuration.
4. The method of claim 1, wherein at least one of the suspension elements comprises a suspension cord.
5. The method of claim 4, wherein the suspension cord comprises at least one strain relief.
6. The method of claim 5, wherein the strain relief comprises a spring.
7. The method of claim 4, wherein the suspension cord comprises Nitinol wire.
8. The method of claim 1, wherein at least one of the soft tissue anchors is anchored to one of the group consisting of: areolar tissue, the pectoralis muscle, and the fascial planes overlying rib and chest wall structures.
9. The method of claim 1, wherein at least one of the soft tissue anchors is a mesh basket.
10. The method of claim 1, wherein at least one of the soft tissue anchors is a polymer tube.
11. The method of claim 1, wherein the support is attached to one of the group consisting of: the first rib, the clavicle, and the manubrium of the sternum.
12. The method of claim 1, further comprising the step of adjusting the tension of the suspension elements after the soft tissue anchors are suspended from the support.
13. The method of claim 1, wherein adjusting the tension of the suspension elements is accomplished non-invasively.
14. The method of claim 1, wherein the support comprises a full ring.
15. The method of claim 1, wherein the support has an elongate shape.
16. The method of claim 1, wherein the suspending the first and second soft tissue anchor steps support the breast mass without cupping the breast mass.
17. The method of claim 1, wherein the first soft tissue anchor comprises a disc.
18. The method of claim 1, wherein after the suspending steps the first soft tissue anchor and the second soft tissue anchor each act independently as point anchoring sources to support the breast tissue.

* * * * *